United States Patent
Thayer et al.

(10) Patent No.: US 6,924,364 B2
(45) Date of Patent: Aug. 2, 2005

(54) HUMAN SECRETED PROTEIN, ZZP1

(75) Inventors: Edward C. Thayer, Seattle, WA (US); Philippa J. Webster, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 171 days.

(21) Appl. No.: 09/922,488

(22) Filed: Aug. 3, 2001

(65) Prior Publication Data

US 2002/0119553 A1 Aug. 29, 2002

Related U.S. Application Data

(60) Provisional application No. 60/222,814, filed on Aug. 4, 2000, and provisional application No. 60/260,512, filed on Jan. 9, 2001.

(51) Int. Cl.$^7$ .................................................. C07K 1/00
(52) U.S. Cl. ....................... 530/853; 530/403; 530/853; 424/185.1; 424/192.1
(58) Field of Search ................................. 530/395, 403, 530/853; 424/185.1, 192.1

(56) References Cited

U.S. PATENT DOCUMENTS

| 6,001,599 A | 12/1999 | Harris et al. ................ 435/69.3 |
| 2004/0033504 A1 * | 2/2004 | Agarwal et al. ................ 435/6 |

FOREIGN PATENT DOCUMENTS

| WO | 01/55319 A2 | 8/2001 | |
| WO | 01/75067 A2 | 10/2001 | |
| WO | 01/81363 A1 | 11/2001 | ........... C07H/21/04 |

OTHER PUBLICATIONS

Public EST, Genbank Accession No. AI208352.1, Mar. 30, 2000.
Public genomic sequence, Genbank Accession No. AP000777, May 30, 2000.
Epifano, O. et al., *Journal of Biological Chemistry* 270(45):27254–27258, 1995.
Public EST, Genbank Accession No. AA426398, 1997.
EST from Incyte Pharmaceuticals, Inc., INC3190411, 1997.
Tentative Human Consensus (TIGR) THC_HT27610, 1997.
Public EST, Genbank Accession No. AA890119, 1998.
EST from Incyte Pharmaceuticals, Inc., INC3418032H2, 1998.
Public EST, Genbank Accession No. AI698605, 1999.
Public EST, Genbank Accession No. AI766401, 1999.
Public EST, Genbank Accession No. BG711776, 2001.

* cited by examiner

*Primary Examiner*—Patrick J. Nolan
(74) *Attorney, Agent, or Firm*—Robyn Adams

(57) ABSTRACT

The present invention relates to polynucleotide and polypeptide molecules, and variants thereof, for Zzp1, a novel Zona Pellucida protein. The polypeptides, and polynucleotides encoding them, are fertility modulating and may be used for delivery and therapeutics. The present invention also includes antibodies to the Zzp1 polypeptides.

7 Claims, No Drawings

HUMAN SECRETED PROTEIN, ZZP1

This application is related to Provisional Applications No. 60/222,814 filed on Aug. 4, 2000, and 60/260,512 filed Jan. 9, 2001. Under 35 U.S.C. § 119(e)(1), this application claims benefit of said Provisional Applications.

BACKGROUND OF THE INVENTION

The zona pellucida is an extracellular matrix that is composed of three glycoproteins, which is a major secretory product of growing oocytes and can also be found on ovulated eggs and early embryos. The fertilized ovum is surrounded by this matrix of mucoproteins, which separates the egg from a layer of follicle cells that provide nourishment to the egg.

Three components of the mouse zona pellucida have been identified (ZP1, ZP2, and ZP3) and contain a signal sequence that directs the protein into a secretory pathway and is cleaved from the mature protein, and a transmembrane domain. In mice these three genes are expressed in a coordinate, oocyte-specific manner during the growth of oogenesis. See, for example, Epifano, O. et al., *Development* 121: 1947–1956, 1995.

In the mouse model of fertilization, the ZP3 protein first binds the sperm, followed by the binding of ZP2. ZP1 then crosslinks ZP3 and ZP2 dimers. The interaction of these three proteins with the sperm result in the induction of the acrosome reaction (Bork, P. et al., *FEBS* 300:237–240, 1992). Thus the zona pellucida plays a critical role in fertilization and the post-fertilization block to polyspermy.

Thus genes of the zona pellucida (ZP) family and their encoded proteins are critical in understanding the process of fertilization. The identification of additional members of this family is needed to study this process and to develop methods to modulate it. The present invention provides a novel member of the zona pellucida proteins and related compositions whose uses will be apparent to those skilled in the art from the teachings herein.

SUMMARY OF THE INVENTION

The invention relates to a novel ZP gene and the polypeptides it encodes.

The Zzp1 polynucleotides, polypeptides, fragments, and antibodies can be useful to modulation sperm-egg binding, fertilization, extracellular matrix formation and immunization. The polynucleotides, polypeptides, antibodies, or fragments thereof can be administered to a mammal to induce transient or permanent sterility.

Within one aspect, the invention provides an isolated polypeptide molecule comprising residues 26 to 546 of SEQ ID NO:2. Within an embodiment, the polypeptide molecule comprises residues 26 to 627 of SEQ ID NO:2. Within another embodiment, the the polypeptide molecule comprises residues 1 to 627 of SEQ ID NO:2. Within another embodiment, the polypeptide molecule also comprises at least nine contiguous amino acid residues of SEQ ID NO:2 are operably linked via a peptide bond or polypeptide linker to a second polypeptide selected from the group consisting of maltose binding protein, an immunoglobulin constant region, and a polyhistidine tag.

Within another embodiment, the polypeptide molecule also comprises a fusion protein wherein polypeptide is conjugated with a compound selected from the group consisting of keyhole limpet hemocyanin, muramyl dipeptide, histidine-tag, beta gal, and palmitic acid. Within another embodiment, is provided an isolated polynucleotide molecule encoding the polypeptide comprising amino acid residues 26 to 546 of SEQ ID NO:2.

Within another aspect, the invention provides an expression vector comprising the following operably linked elements: a) a transcription promoter; b) a DNA segment encoding the polypeptide comprising amino acid residues 26 to 546 of SEQ ID NO:2; and c) a transcription terminator. Within another embodiment, the DNA segment further encodes an affinity tag. Within another embodiment, the invention provides a cultured cell into which has been introduced the expression vector, wherein said cell expresses the polypeptide encoded by the DNA segment. Within another embodiment, is provided a method of producing a polypeptide comprising culturing the cell, whereby said cell expresses the polypeptide encoded by the DNA segment, and recovering the polypeptide. Within another embodiment, the polypeptide made by the method is also provided.

Within another aspect, the invention provides a method of producing an antibody to a polypeptide comprising the following steps: inoculating an animal with the polypeptide such that the polypeptide elicits an immune response in the animal to produce the antibody; and isolating the antibody from the animal, wherein the polypeptide is chosen from, a polypeptide comprising residues 26 to 546 of SEQ ID NO:2; a polypeptide comprising residues 26 to 627 of SEQ ID NO:2; and a polypeptide comprising residues 1 to 627 of SEQ ID NO:2 and wherein the antibody produced by the method specifically binds to a polypeptide of SEQ ID NO:2. Within another embodiment, the antibody produced by the method is also provided. Within another embodiment, the invention provides a method of producing an antibody to a polypeptide comprising the following steps: inoculating an animal with the polypeptide such that the polypeptide elicits an immune response in the animal to produce the antibody; and isolating the antibody from the animal, wherein the polypeptide comprises at least fifteen consecutive amino acids of the amino acid sequence as shown in SEQ ID NO:2, and wherein the antibody produced by the method specifically binds to a polypeptide of SEQ ID NO:2. Within another embodiment, the antibody produced by the method is provided.

Within another aspect, the invention provides a method for inhibiting sperm-oocyte fusion comprising contacting the sperm and oocytes with the polypeptide comprising the amino acid residues of SEQ ID NO:2., or a fragment thereof, whereby the polypeptide or fragment inhibits the sperm and oocyte fusion.

Within another aspect, the invention provides a method for inhibiting sperm-oocyte fusion comprising contacting the sperm and oocytes with the antibodies described herein, whereby the polypeptide or fragment inhibits the sperm and oocyte fusion.

Within another aspect, the invention provides a method for inducing infertility in a mammal, comprising administering to the mammal an contraceptively effective dose of the polypeptide the comprising amino acid residues of SEQ ID NO:2., or a fragment thereof, wherein the polypeptide induces an immune response in the mammal, thereby inducing infertility in the mammal.

Within another aspect, the invention provides a method for inducing infertility in a mammal, comprising administering to the mammal antibodies as described herein, wherein the polypeptide induces an immune response in the mammal, thereby inducing infertility in the mammal.

Within another aspect, the invention provides a composition comprising a contraceptive dose of the polypeptide comprising the amino acid as shown in SEQ ID NO:2., or a fragment thereof, and an acceptable carrier, and/or adjuvant.

These and other aspects of the invention will become evident upon reference to the following detailed description of the invention and attached drawings.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985) (SEQ ID NO:7), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5'CCCGTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" or "species homolog", denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based upon the discovery of a novel cDNA sequence (SEQ ID NO:1) and corresponding polypeptide having homology to murine zona pellucida 1 (ZP1). See, for example, Epifano, O. et al., *Development* 11: 1947–1956, 1995. Also called "Zona" genes, members of this family include ZP2 and ZP3, which are also termed, sperm receptors (Bork, P. et al., *FEBS* 300:237–240, 1992). Polynucleotides and polypeptides of the present invention have been designated Zona Pellucida 1 and is termed herein, Zzp1.

Examination of the Zzp1 deduced amino acid sequence (SEQ ID NO:2) permitted identification of multiple domains. The first domain is a secretory peptide domain, beginning with residue 1 and ending with residue 25 of SEQ ID NO:2. Additionally, there is a "trefoil" domain from residue 232 to residue 270 of SEQ ID NO:2, and a zona pellucida domain from residue 276 to 546 of SEQ ID NO:2; and a transmembrane domain from amino acid residue 593 to amino acid residue 627 of SEQ ID NO:2. An alternative transmembrane domain is from amino acid residue 598 to amino acid residue 621 of SEQ ID NO:2. Additionally there is a potential furin processing site at residues 549 to 553 of SEQ ID NO:2. Thus a soluble form of Zzp1 would comprise residue 26 to residue 548, for example. Additionally, potential N-linked glycosylation sites are at residues 376 to 378, residue 558 to 560, and residues 593 to 595.

Analysis of the tissue distribution of Zzp1 can be performed by the Northern blotting technique using Human Multiple Tissue and Master Dot Blots. Such blots are commercially available (Clontech, Palo Alto, Calif.) and can be probed by methods known to one skilled in the art. Also see, for example, Wu W. et al., Methods in Gene Biotechnology, CRC Press LLC, 1997. Such PCR analysis indicated that Zzp1 is expressed in pituitary, prostate, salivary gland, small intestine, testis, islet, and placenta tissues. Additionally, portions of the polynucleotides of the present invention can be identified by querying sequence databases and identifying the tissues from which the sequences are derived. Portions of the polynucleotides of the present invention have been identified in pituitary, thymus, brain, and testis cDNA libraries.

The present invention provides polynucleotide molecules, including DNA and RNA molecules, that encode the Zzp1 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the Zzp1 polypeptide of SEQ ID NO:2. Those skilled in the art will recognize that the degenerate sequence of SEQ ID NO:3 provides all RNA sequences encoding SEQ ID NO:2 by substituting U for T. Thus, Zzp1 polypeptide-encoding polynucleotides comprising nucleotide 1 to nucleotide 1905 of SEQ ID NO:3, and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto under stringent conditions. Polynucleotide hybridization is well known in the art and widely used for many applications, see for example, Sambrook et al., *Molecular Cloning: A Laboratory Manual, Second Edition*, Cold Spring Harbor, N.Y., 1989; Ausubel et al., eds., *Current Protocols in Molecular Biology*, John Wiley and Sons, Inc., NY, 1987; Berger and Kimmel, eds., Guide to Molecular Cloning Techniques, *Methods in Enzymology*, volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

As an illustration, a nucleic acid molecule encoding a variant Zzp1 polypeptide can be hybridized with a nucleic acid molecule having the nucleotide sequence of SEQ ID NO:1 (or their complements) at 42° C. overnight in a solution comprising 50% formamide, 5×SSC (1×SSC: 0.15 M sodium chloride and 15 mM sodium citrate), 50 mM sodium phosphate (pH 7.6), 5×Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., ExpressHyb™ Hybridization Holution from CLONTECH Laboratories, Inc., Palo Alto, Calif.) according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant Zzp1 polypeptide hybridize with a nucleic acid molecule having the nucleotide sequences of SEQ ID NO:1 (or its complement) under stringent washing conditions, in which the wash stringency is equivalent to 0.5×–2×SSC with 0.1% SDS at 55–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

The present invention also contemplates Zzp1 variant nucleic acid molecules that can be identified using two criteria: a determination of the similarity between the encoded polypeptides with the amino acid sequences of SEQ ID NO:2 (as described below), and a hybridization assay, as described above. Such Zzp1 variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., and (2) that encode a polypeptide having at least 80%, preferably 90%, more preferably, 95% or greater than 95% sequence identity to the amino acid sequence of SEQ ID NOs:2 or 4. Alternatively, Zzp1 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., and (2) that encode a polypeptide having at least 80%, preferably 90%, more preferably 95% or greater than 95% sequence identity to the amino acid sequence of SEQ ID NO:2.

The highly conserved amino acids in the trefoil, or zona pellucida domains of Zzp1 can be used as a tool to identify new family members. For instance, reverse transcription-polymerase chain reaction (RT-PCR) can be used to amplify sequences encoding the conserved trefoil or zona pellucida domain from RNA obtained from a variety of tissue sources or cell lines. In particular, highly degenerate primers designed from the Zzp1 sequences are useful for this purpose.

As previously noted, the isolated polynucleotides of the present invention include DNA and RNA. Methods for preparing DNA and RNA are well known in the art. In general, RNA is isolated from a tissue or cell that produces large amounts of Zzp1 RNA. Such tissues and cells can be identified by Northern blotting (Thomas, *Proc. Natl. Acad. Sci. USA* 77:5201, 1980), and include pituitary, thymus, brain, and testis.

Total RNA can be prepared using guanidine isothiocyante extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–12, 1972). Complementary DNA (cDNA) is prepared from poly(A)$^+$ RNA using known methods. In the alternative, genomic DNA can be isolated. Polynucleotides encoding Zzp1 polypeptides are then identified and isolated by, for example, hybridization or PCR.

A full-length clone encoding Zzp1 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron.

Methods for preparing cDNA and genomic clones are well known and within the level of ordinary skill in the art, and include the use of the sequence disclosed herein, or parts thereof, for probing or priming a library. Expression libraries can be probed with antibodies to Zzp1 or other specific binding partners.

Zzp1 polynucleotide sequences disclosed herein can also be used as probes or primers to clone 5' non-coding regions of a Zzp1 gene. In view of the tissue-specific expression discussed above, this gene region is expected to provide for specific expression in pituitary, thymus, brain, and testis. Additionally, as the mouse ZP1 protein is expressed in ovary and oocytes in specific, the Zzp1 gene is expected to also be expressed in the tissues, as well. Promoter elements from a Zzp1 gene could thus be used to direct the tissue-specific expression of heterologous genes in, for example, transgenic animals or patients treated with gene therapy. Cloning of 5' flanking sequences also facilitates production of Zzp1 proteins by "gene activation" as disclosed in U.S. Pat. No. 5,641,670. Briefly, expression of an endogenous Zzp1 gene in a cell is altered by introducing into the Zzp1 locus a DNA construct comprising at least a targeting sequence, a regulatory sequence, an exon, and an unpaired splice donor site. The targeting sequence is a Zzp1 5' non-coding sequence that permits homologous recombination of the construct with the endogenous Zzp1 locus, whereby the sequences within the construct become operably linked with the endogenous Zzp1 coding sequence. In this way, an endogenous Zzp1 promoter can be replaced or supplemented with other regulatory sequences to provide enhanced, tissue-specific, or otherwise regulated expression.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323–356 (1984) and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are Zzp1 polypeptides from other mammalian species, including porcine, ovine, bovine, canine, feline, equine, and primate polypeptides. Orthologs of human Zzp1 can be cloned using information and compositions provided by the present invention in combination with conventional cloning techniques. For example, a cDNA can be cloned using mRNA obtained from a tissue or cell type that expresses Zzp1 as disclosed herein. Such tissue would include, for example, pituitary, thymus, brain, testis, ovary, prostate, salivary gland, small intestine, islet, and placenta. Suitable sources of mRNA can be identified by probing Northern blots with probes designed from the sequences disclosed herein. A library is then prepared from mRNA of a positive tissue or cell line. A Zzp1-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human Zzp1 sequences disclosed herein. Within an additional method, the cDNA library can be used to transform or transfect host cells, and expression of the cDNA of interest can be detected with an antibody to Zzp1 polypeptide. Similar techniques can also be applied to the isolation of genomic clones. The murine ortholog of Zzp1 has been identified. See Epifano, ibid.

Those skilled in the art will recognize that the sequences disclosed in SEQ ID NO:1 represent a single allele of human Zzp1 and that allelic variation and alternative splicing are expected to occur. Allelic variants of this sequence can be cloned by probing cDNA or genomic libraries from different individuals according to standard procedures. Allelic variants of the DNA sequences shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the Zzp1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated Zzp1 polypeptides that are substantially similar to the polypeptides of SEQ ID NO:2 and their orthologs. Such polypeptides will be at least 70% identical, or more identical to SEQ ID NO:2 and their orthologs. The present invention also includes polypeptides that comprise an amino acid sequence having at least 75%, at least 80%, at least 85%, at least 90% or greater than 95% sequence identity to the zona pellucida domain, (i.e., residues 279 to 546 of SEQ ID NO:2) or to the trefoil domain (i.e., residue 232 to 270 of SEQ ID NO:2). Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant Zzp1. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequences of SEQ ID NO:2. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than –1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in an Zzp1 gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The ability of such variants to promote cell-cell interactions can be determined using a standard method, such as the assay described herein.

Alternatively, a variant Zzp1 polypeptide can be identified by the ability to specifically bind anti-Zzp1 antibodies.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of receptor-ligand interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related sperm receptor molecules, i.e., ZP2, ZP3, and murine ZP1.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed Zzp1 DNA and polypeptide sequences can be generated through DNA shuffling, as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., receptor-ligand binding) can be recovered from the host cells and rapidly sequenced using modem equipment. These methods allow the rapid determination of the importance of individual amino acid residues in a polypeptide of interest, and can be applied to polypeptides of unknown structure.

Regardless of the particular nucleotide sequence of a variant Zzp1 gene, the gene encodes a polypeptide that is characterized by its cell-cell interaction activity, or by the ability to bind specifically to an anti-Zzp1 antibody. More specifically, variant Zzp1 genes encode polypeptides which exhibit at least 50%, and preferably, greater than 70, 80, or 90%, of the activity of polypeptide encoded by the human Zzp1 gene described herein.

Variant Zzp1 polypeptides or substantially homologous Zzp1 polypeptides are characterized as having one or more amino acid substitutions, deletions or additions. These changes are preferably of a minor nature, that is conservative amino acid substitutions and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from 775 to 2000 amino acid residues that comprise a sequence that is at least 85%, preferably at least 90%, and more preferably 95% or more identical to the corresponding region of SEQ ID NO:2. Polypeptides comprising affinity tags can further comprise a proteolytic cleavage site between the Zzp1 polypeptide and the affinity tag. Preferred such sites include thrombin cleavage sites and factor Xa cleavage sites.

For any Zzp1 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zzp1 variants based upon the nucleotide and amino acid sequences described herein. Accordingly, the present invention includes a computer-readable medium encoded with a data structure that provides at least one of the following sequences: SEQ ID NO:1, SEQ ID NO:2, and SEQ ID NO:3. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention further provides a variety of other polypeptide fusions and related multimeric proteins comprising one or more polypeptide fusions. For example, a zona pellucida domain can be prepared as a fusion to a dimerizing protein, as disclosed in U.S. Pat. Nos. 5,155,027 and 5,567,584. Preferred dimerizing proteins in this regard include other zona pellucida domains, zona pellucida polypeptide fragments, or polypeptides comprising other members of the sperm receptor family of proteins, such as, for example, ZP2 and ZP3. These zona pellucida domain fusions, zona pellucida polypeptide fragment fusions, or fusions with other Zona pellucida proteins can be expressed in genetically engineered cells to produce a variety of multimeric zona pellucida-like analogs.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between Zzp1 of the present invention with the functionally equivalent domain(s) from another family member, such as ZP2, ZP3, and murine Zp1. Such domains include, but are not limited to, conserved motifs such as the zona pellucida domain, and the trefoil domain. Such fusion proteins would be expected to have a biological functional profile that is the same or similar to polypeptides of the present invention or other known sperm receptor family proteins (e.g. ZP2 and ZP3, and ZP1), depending on the fusion constructed. Moreover, such fusion proteins may exhibit other properties as disclosed herein.

Moreover, using methods described in the art, polypeptide fusions, or hybrid Zzp1 proteins, are constructed using regions or domains of the inventive Zzp1 in combination with those of other zona pellucida and trefoil-like molecules. (e.g. ZP2 and ZP3), or heterologous proteins (Sambrook et al., ibid., Altschul et al., ibid., Picard, Cur. Opin. Biology, 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Auxiliary domains can be fused to Zzp1 polypeptides to target them to specific cells, tissues, or macromolecules (e.g., pituitary, thymus, brain, testis, ovary, prostate, salivary gland, small intestine, islet, and placenta). For example, a trefoil polypeptide domain, or trefoil polypeptide fragment or protein, could be targeted to a predetermined cell type by fusing it to a zona pellucida domain or fragment that specifically binds to a sperm polypeptide. In this way, polypeptides, polypeptide fragments and proteins can be targeted for therapeutic or diagnostic purposes. Such zona pellucida or trefoil polypeptide domains or fragments can be fused to two or more moieties, such as an affinity tag for purification and a targeting-zona pellucida domain. Polypeptide fusions can also comprise one or more cleavage sites, particularly between domains. See, Tuan et al., *Connective Tissue Research* 34:1–9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of Zzp1 polypeptide can be fused to *E. coli* β-galactosidase (1,021 residues; see Casadaban et al., J. Bacteriol. 143:971–980, 1980), a 10-residue spacer, and a 4-residue factor Xa cleavage site. In a second example, residues of Zzp1 polypeptide can be fused to maltose binding protein (approximately 370 residues), a 4-residue cleavage site, and a 6-residue polyhistidine tag.

To direct the export of a Zzp1 polypeptide from the host cell, the Zzp1 DNA is linked to a second DNA segment encoding a secretory peptide, such as a t-PA secretory peptide or a Zzp1 secretory peptide. To facilitate purification of the secreted polypeptide, a C-terminal extension, such as a poly-histidine tag, substance P, Flag peptide (Hopp et al., *Bio/Technology* 6:1204–1210, 1988; available from Eastman Kodak Co., New Haven, Conn.), maltose binding protein, or another polypeptide or protein for which an antibody or other specific binding agent is available, can be fused to the Zzp 1 polypeptide.

The present invention also includes "functional fragments" of Zzp1 polypeptides and nucleic acid molecules encoding such functional fragments. Routine deletion analyses of nucleic acid molecules can be performed to obtain functional fragments of a nucleic acid molecule that encodes an Zzp1 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for cell-cell interactions, or for the ability to bind anti-Zzp1 antibodies. One alternative to exonuclease digestion is to use oligonucleotide-directed mutagenesis to introduce deletions or stop codons to specify production of a desired fragment. Alternatively, particular fragments of an Zzp1 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems*, Cantell (ed.), pages 65–72 (Nijhoff 1987), Herschman, "The EGF Receptor," in *Control of Animal Cell Proliferation*, Vol. 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a Zzp1 gene that have amino acid changes, compared with the amino acid sequence of SEQ ID NO:2. A variant Zzp1 gene can be identified on the basis of structure by determining the level of identity with nucleotide and amino acid sequences of SEQ ID NOs:1, and 2, as discussed above. An alternative approach to identifying a variant gene on the basis of structure is to determine whether a nucleic acid molecule encoding a potential variant Zzp1 gene can hybridize to a nucleic acid molecule having the nucleotide sequence of SEQ ID NO:1, as discussed above.

Using the methods discussed herein, one of ordinary skill in the art can identify and/or prepare a variety of polypeptide fragments or variants of SEQ ID NO:2 or that retain the zona pellucida and/or trefoil activity of the wild-type Zzp1 protein. Such polypeptides may include additional amino acids from, for example, a secretory domain, a protease domain, a zona pellucida domain, part or all of a transmembrane and intracellular domains, including amino acids responsible for intracellular signaling; fusion domains; affinity tags; and the like.

The present invention also provides polypeptide fragments or peptides comprising an epitope-bearing portion of an Zzp1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, preferably at least ten to fifteen amino acids, more preferably 15 to 30 amino acids of SEQ ID NO:2. Such epitope-bearing peptides and polypeptides can be produced by fragmenting a Zzp1 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105–116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

As an illustration, potential antigenic sites in Zzp1 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The results of this analysis indicated that a peptide consisting of amino acid residue 31 to residue 37 of SEQ ID NO:2; residue 28 to residue 42 of SEQ ID NO:2; residue 63 to residue 70 of SEQ ID NO:2; residue 31 to residue 37 of SEQ ID NO:2; residue 63 to residue 75 of SEQ ID NO:2; residue 82 to residue 87 of SEQ ID NO:2; residue 94 to residue 107 of SEQ ID NO:2; residue 100 to residue 107 of SEQ ID NO:2; residue 117 to residue 126 of SEQ ID NO:2; residue 132 to residue 146 of SEQ ID NO:2; residue 133 to residue 141 of SEQ ID NO:2; residue 163 to residue 172 of SEQ ID NO:2; residue 178 to residue 189 of SEQ ID NO:2; residue 179 to residue 184 of SEQ ID NO:2; residue 191 to residue 201 of SEQ ID NO:2; residue 216 to residue 223 of SEQ ID NO:2; residue 228 to residue 234 of SEQ ID NO:2; residue 243 to residue 254 of SEQ ID NO:2; residue 245 to residue 252 of SEQ ID NO:2; residue 256 to residue 265 of SEQ ID NO:2; residue 257 to residue 263 of SEQ ID NO:2; residue 277 to residue 282 of SEQ ID NO:2; residue 308 to residue 318 of SEQ ID NO:2; residue 354 to residue 367 of SEQ ID NO:2; residue 355 to residue 366 of SEQ ID NO:2; residue 390 to residue 424 of SEQ ID NO:2; residue 418 to residue 423 of SEQ ID NO:2; residue 428 to residue 435 of SEQ ID NO:2; residue 439 to residue 446 of SEQ ID NO:2; residue 441 to residue 445 of SEQ ID NO:2; residue 457 to residue 466 of SEQ ID NO:2; residue 472 to residue 484 of SEQ ID NO:2; residue 476 to residue 483 of SEQ ID NO:2; residue 510 to residue 519 of SEQ ID NO:2; residue 511 to residue 517 of SEQ ID NO:2; residue 527 to residue 541 of SEQ ID NO:2; residue 534 to residue 540 of SEQ ID NO:2; residue 543 to residue 596 of SEQ ID NO:2; residue 549 to residue 567 of SEQ ID NO:2; residue 576 to residue 584 of SEQ ID NO:2; residue 588 to residue 599 of SEQ ID NO:2; and residue 629 to residue 635 of SEQ ID NO:2.

Hydrophilic peptides, such as those predicted by one of skill in the art from a hydrophobicity plot are also immunogenic. Zzp1 hydrophilic peptides include peptides comprising amino acid sequences selected from the group consisting of: residues 27 to 37 of SEQ ID NO:2; residues 52 to 57 of SEQ ID NO:2; residues 62 to 72 of SEQ ID NO:2; residues 80 to 92 of SEQ ID NO:2; residues 95 to 108 of SEQ ID NO:2; residues 133 to 144 of SEQ ID NO:2; residues 164 to 188 of SEQ ID NO:2; residue 192 to residue 200 of SEQ ID NO:2; residue 207 to 235 of SEQ ID NO:2; residue 216 to 224 of SEQ ID NO:2; residue 245 to 253 of SEQ ID NO:2; residue 245 to 270 of SEQ ID NO:2; residue 275 to 280 of SEQ ID NO:2; residue 309 to 317 of SEQ ID NO:2; residue 352 to 368 of SEQ ID NO:2; residue 392 to 402 of SEQ ID NO:2; residue 407 to 424 of SEQ ID NO:2; residue 413 to 421 of SEQ ID NO:2; residue 438 to 444 of SEQ ID NO:2; residue 455 to 470 of SEQ ID NO:2; residue 475 to 484 of SEQ ID NO:2; residue 493 to 502 of SEQ ID NO:2; residue 512 to 519 of SEQ ID NO:2; residue 544 to 568 of SEQ ID NO:2; residue 547 to 562 of SEQ ID NO:2; residue 572 to 594 of SEQ ID NO:2; residue 589 to 594 of SEQ ID NO:2; and residue 624 to 635 of SEQ ID NO:2. Regions of the polypeptide, which are likely to be on the surface of the folded protein, are also likely to be antigenic. These regions include the amino acid from residue 27 to 37 of SEQ ID NO:2; residue 82 to 87 of SEQ ID NO:2; residue 134 to 141 of SEQ ID NO:2; residue 165 to 170 of SEQ ID NO:2; residue 216 to 223 of SEQ ID NO:2; residue 360 to 365 of SEQ ID NO:2; residue 390 to 400 of SEQ ID NO:2; residue 418 to 442 of SEQ ID NO:2; residue 459 to 467 of SEQ ID NO:2; residue 478 to 484 of SEQ ID NO:2; residue 494 to 500 of SEQ ID NO:2; residue 546 to 564 of SEQ ID NO:2; residue 576 to 584 of SEQ ID NO:2; and residue 628 to 635 of SEQ ID NO:2.

Zzp1 polypeptides can also be used to prepare antibodies that specifically bind to Zzp1 epitopes, peptides or polypeptides. The Zzp1 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a Zzp1 polypeptide (e.g., SEQ ID NO:2). Polypeptides comprising a larger portion of a Zzp1 polypeptide, i.e., from 30 to 10 residues up to the entire length of the amino acid sequence are included. Antigens or immunogenic epitopes can also include attached tags, adjuvants and carriers, as described herein. Suitable antigens include the Zzp1 polypeptides encoded by SEQ ID NO:2 from amino acid number 232 to amino acid number 270; form amino acid number 276 to amino acid number 546; or a contiguous 9 to 635 amino acid fragment thereof. Other suitable antigens include residue 1 to residue 25, of SEQ ID NO:2; residue 26 to residue 231 of SEQ ID NO:2; residue 547 to residue 592 of SEQ ID NO:2; residue 593 to reside 635; and residue 593 to residue 627 of SEQ ID NO:2. Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a Zzp1 polypeptide or a fragment thereof. The immunogenicity of a Zzp1 polypeptide may be increased through the use of an adjuvant, such as alum (aluminum hydroxide) or Freund's complete or incomplete adjuvant. Polypeptides useful for immunization also include fusion polypeptides, such as fusions of Zzp1 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to Zzp1 protein or peptide, and selection of antibody display libraries in phage or similar vectors (for instance, through use of immobilized or labeled Zzp1 protein or peptide). Genes encoding polypeptides having potential Zzp1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis.

These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from CLONTECH Laboratories, Inc., (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zzp1 sequences disclosed herein to identify proteins which bind to Zzp1. These "binding proteins" which interact with Zzp1 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zzp1 "antagonists" to block Zzp1 binding and signal transduction in vitro and in vivo. These anti-Zzp1 binding proteins would be useful for modulating, for example, platelet aggregation, apoptosis, neurogenesis, myogenesis, immunologic recognition, tumor formation, and cell-cell interactions in general.

Antibodies are determined to be specifically binding if they exhibit a threshold level of binding activity (to a Zzp1) polypeptide, peptide or epitope) of at least 10-fold greater than the binding affinity to a control (non-Zzp1) polypeptide. The binding affinity of an antibody can be readily determined by one of ordinary skill in the art, for example, by Scatchard analysis (Scatchard, G., *Ann. NY Acad. Sci.* 51: 660–672, 1949).

A variety of assays known to those skilled in the art can be utilized to detect antibodies which specifically bind to Zzp1 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant Zzp1 protein or polypeptide.

Antibodies to Zzp1 may be used for tagging cells that express Zzp1; for isolating Zzp1 by affinity purification; for diagnostic assays for determining circulating levels of Zzp1 polypeptides; for detecting or quantitating soluble Zzp1 as marker of underlying pathology or disease; in analytical methods employing FACS; for screening expression libraries; for generating anti-idiotypic antibodies; and as neutralizing antibodies or as antagonists to block Zzp1 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to Zzp1 or fragments thereof may be used in vitro to detect denatured Zzp1 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (sperm or antigen, respectively, for instance). More specifically, Zzp1 polypeptides or anti-Zzp1 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer-+ cells or tissues). Alternatively, a fusion protein including only the zona pellucida domain may be suitable for directing a detectable molecule, a cytotoxic molecule or a complementary molecule to a cell or tissue type of interest. Similarly, the corresponding binding protein (i.e., a sperm molecule, anti-Zzp1 antibody, or ZP2 or ZP3) to Zzp1 can be conjugated to a detectable or cytotoxic molecule and provide a generic targeting vehicle for cell/tissue-specific delivery of generic anti-complementary-detectable/cytotoxic molecule conjugates.

In another embodiment, Zzp1-cytokine fusion proteins or antibody-cytokine fusion proteins can be used for enhancing in vivo killing of target tissues (for example, pituitary, thymus, brain, testis, ovary, prostate, salivary gland, small intestine, islet, and placenta), if the Zzp1 polypeptide or anti-Zzp1 antibody targets hyperproliferative tissues from these organs. See, generally, Homick et al., (*Blood* 89:4437–47, 1997) who described fusion proteins that enable targeting of a cytokine to a desired site of action, thereby providing an elevated local concentration of cytokine. Suitable Zzp1 polypeptides or anti-Zzp1 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

The bioactive polypeptide or antibody conjugates described herein can be delivered intravenously, intraarterially or intraductally, or may be introduced locally at the intended site of action.

The Zzp1 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a Zzp1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zzp1 polypeptide into the secretory pathway of a host cell, a secretory signal sequence (also known as a leader sequence, prepro sequence or pre sequence) is provided in the expression vector. The secretory signal sequence may be that of Zzp1, or may be derived from another secreted protein (e.g., t-PA) or synthesized de novo. The secretory signal sequence is operably linked to the Zzp1 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The native secretory signal sequence of the polypeptides of the present invention is used to direct other polypeptides into the secretory pathway. The present invention provides for such fusion polypeptides. A signal fusion polypeptide can be made wherein a secretory signal sequence derived from a Zzp1 polypeptide is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Alternatively, the trefoil domain of Zzp1 can be substituted by a heterologous sequence providing a different trefoil domain. In this case, the fusion product can be secreted, and the zona pellucida domain of Zzp1 can direct the trefoil domain to a specific tissue described above. This substituted trefoil domain can be chosen from the trefoil domains represented by the ZP protein families, or domains from other known trefoil proteins. Similarly, the zona pellucida domain of Zzp1 protein can be substituted by a heterlogous sequence providing a different zona pellucida domain. Again, the fusion product can be secreted and the substituted zona pellucida domain can target the trefoil domain of Zzp1 to a specific tissue. The substituted zona pellucida domain can be chosen from the zona pellucida domains of the ZP protein families. In these cases, the fusion products can be soluble or membrane-anchored proteins. Other proteins having a trefoil domain are for example, Spasmolytic polypeptide, and Intestinal Trefoil Factor.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J*. 1:841–5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica nuclear polyhedrosis virus* (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant Zzp1 baculovirus utilizes a transposon-based system described by Luckow (Luckow, V. A, et al., *J Virol* 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the Zzp1 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case Zzp1. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol Chem* 270:1543–9, 1995. In such transfer vector constructs, a short or long version of the basic protein promoter can be used. Moreover, transfer vectors can be constructed which replace the native Zzp1 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native Zzp1 secretory signal sequence. In addition, transfer vectors can include an in-frame fusion with DNA encoding an epitope tag at the C- or N-terminus of the expressed Zzp1 polypeptide, for example, a Glu-Glu epitope tag (Grussenmeyer, T. et al., *Proc. Natl. Acad. Sci.* 82:7952–4, 1985). Using a technique known in the art, a transfer vector containing Zzp1 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses Zzp1 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately 2–5×10⁵ cells to a density of 1–2×10⁶ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D)., ibid.). Subsequent purification of the Zzp1 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillemondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. The use of *Pichia methanolica* as host for the production of recombinant proteins is disclosed in U.S. Pat. Nos. 5,716,808, 5,736,383, 5,854,039, and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a Zzp1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for Zzp1 amino acid residues.

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant Zzp1 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

The polypeptides of the present invention can be isolated by a combination of procedures including, but not limited to, anion and cation exchange chromatography, size exclusion, and affinity chromatography. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

Zzp1 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, Zzp1 proteins can be prepared as monomers or multimers; glycosylated or non-glycosylated; pegylated or non-pegylated; and may or may not include an initial methionine amino acid residue.

The activity of Zzp1 polypeptides can be measured using a variety of assays that measure, for example, fertilization, cell-cell fusion; extracellular matrix formation or remodeling; metastasis, and other biological functions associated with zona pellucida family members or with sperm/oocyte interactions. Of particular interest is a change in sperm/egg binding. Assays measuring sperm/egg binding are well known in the art.

Proteins, including alternatively spliced peptides, of the present invention are useful for fertilization, contraception, oocyte and embryo maturation, tumor suppression, immunologic recognition, and growth and differentiation either working in isolation, or in conjunction with other molecules (growth factors, cytokines, etc.) in pituitary, thymus, brain, testis, ovary, prostate, salivary gland, small intestine, islet, and placenta. Alternative splicing of Zzp1 may cell-type specific and confer activity to specific tissues.

Another assay of interest measures or detects changes in proliferation, differentiation, and development of the developing ovum. Additionally, the effects of a Zzp1 polypeptides on cell-cell interactions of immune cells, gamete cells or cells, in general, of a reproductive nature, and tumor cells would be of interest to measure.

Proliferation can be measured using cultured oocytes or in vivo by administering molecules of the claimed invention to an appropriate animal model. Generally, proliferative effects are observed as an increase in cell number and therefore, may include inhibition of apoptosis, as well as mitogenesis. Cultured cells include cell derived from pituitary, thymus, brain, testis, ovary, prostate, salivary gland, small intestine, islet, and placenta from primary cultures. Established cell lines include: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992) and LNCap.FGC adenocarcinoma cells (ATCC No. CRL-1740). Assays measuring cell proliferation are well known in the art. For example, assays measuring proliferation include such assays as chemosensitivity to neutral red dye (Cavanaugh et al., *Investigational New Drugs* 8:347–354, 1990), incorporation of radiolabelled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988).

To determine if Zzp1 is a chemotractant in vivo, Zzp1 can be given by intradermal or intraperitoneal injection. Characterization of the accumulated leukocytes at the site of injection can be determined using lineage specific cell surface markers and fluorescence immunocytometry or by immunohistochemistry (Jose, *J. Exp. Med.* 179:881–87, 1994). Release of specific leukocyte cell populations from bone marrow into peripheral blood can also be measured after Zzp1 injection.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors and receptor-like complementary molecules. The stage of a cell population's differentiation is monitored by identification of markers present in the cell population. For example, myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. The novel polypeptides of the present invention are useful for studies to isolate pituitary, thymus, brain, testis, ovary, prostate, salivary gland, small intestine, islet, and placenta both in vivo and ex vivo.

There is evidence to suggest that factors that stimulate specific cell types down a pathway towards terminal differentiation or dedifferentiation affect the entire cell population originating from a common precursor or stem cell. Thus, Zzp1 polypeptides may stimulate inhibition or proliferation of endocrine and exocrine cells of the pituitary, thymus, brain, testis, ovary, prostate, salivary gland, small intestine, islet, and placenta.

Molecules of the present invention may, while stimulating proliferation or differentiation of pituitary, thymus, brain, testis, ovary, prostate, salivary gland, small intestine, islet, and placenta, inhibit proliferation or differentiation. The novel polypeptides of the present invention are useful to study neural and epithelial stem cells and pituitary, thymus, brain, testis, ovary, prostate, salivary gland, small intestine, islet, and placenta progenitor cells, both in vivo and ex vivo.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989).0

The Zzp1 polypeptides of the present invention can be used to study proliferation or differentiation in pituitary, thymus, brain, testis, ovary, prostate, salivary gland, small intestine, islet, and placenta. Such methods of the present invention generally comprise incubating cells derived from these tissues in the presence and absence of Zzp1 polypeptide, monoclonal antibody, agonist or antagonist thereof and observing changes in cell proliferation or differentiation. Cell lines from these tissues are commercially available from, for example, American Type Culture Collection (Manasas, Va.).

Proteins, including alternatively spliced peptides, and fragments, of the present invention are useful for studying cell-cell fusion, fertilization, development, immune recognition, growth control, tumor suppression, and gamete maturation. Zzp1 molecules, variants, and fragments can be applied in isolation, or in conjunction with other molecules (growth factors, cytokines, etc.) in pituitary, thymus, brain, testis, ovary, prostate, salivary gland, small intestine, islet, and placenta.

Proteins of the present invention are useful for delivery of therapeutic agents such as, but not limited to, proteases, radionuclides, chemotherapy agents, and small molecules. Effects of these therapeutic agents can be measured in vitro using cultured cells, ex vivo on tissue slices, or in vivo by administering molecules of the claimed invention to the appropriate animal model. An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

As a soluble or cell-surface protein, the activity of Zzp1 polypeptide or a peptide to which Zzp1 binds, can be measured by a silicon-based biosensor microphysiometer which measures the extracellular acidification rate or proton excretion associated with cell-surface protein interactions and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including Zzp1 proteins, their, agonists, and antagonists. Preferably, the microphysiometer is used to measure responses of a Zzp1-responsive eukaryotic cell, compared to a control eukaryotic cell that does not respond to Zzp1 polypeptide. Zzp1-responsive eukaryotic cells comprise cells into which a polynucleotide for Zzp1 has been transfected creating a cell that is responsive to Zzp1; or cells naturally responsive to Zzp1. Differences, measured by a change in the response of cells exposed to Zzp1 polypeptide, relative to a control not exposed to Zzp1, are a direct measurement of Zzp1-modulated cellular responses. Moreover, such Zzp1-modulated responses can be assayed under a variety of stimuli. The present invention provides a method of identifying agonists and antagonists of Zzp1 protein, comprising providing cells responsive to a Zzp1 polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of Zzp1 polypeptide and the absence of a test compound provides a positive control for the Zzp1-responsive cells, and a control to compare the agonist activity of a test compound with that of the Zzp1 polypeptide. Antagonists of Zzp1 can be identified by exposing the cells to Zzp1 protein in the presence and absence of the test compound, whereby a reduction in Zzp1-stimulated activity is indicative of agonist activity in the test compound.

Moreover, Zzp1 can be used to identify cells, tissues, or cell lines which respond to a Zzp1-stimulated pathway. The microphysiometer, described above, can be used to rapidly identify cells responsive to Zzp1 of the present invention. Cells can be cultured in the presence or absence of Zzp1 polypeptide. Those cells, which elicit a measurable change in extracellular acidification in the presence of Zzp1, are responsive to Zzp1. Such cell lines, can be used to identify variants, antagonists and agonists of Zzp1 polypeptide as described above. Using similar methods, cells expressing Zzp1 can be used to identify cells, which stimulate a Zzp1-signaling pathway.

In view of the tissue distribution (pituitary, thymus, brain, testis, ovary, prostate, salivary gland, small intestine, islet, and placenta) observed for Zzp1 expression, agonists (including the native zona pellucida and trefoil domains) and antagonists have enormous potential in both in vitro and in vivo applications. Compounds identified as Zzp1 agonists and antagonists are useful for studying fertilization, tumor proliferation and suppression, and extracellular matrix proteins, in vitro and in vivo. For example, Zzp1 and agonist compounds are useful as components of defined cell culture media, and may be used alone or in combination with other cytokines and hormones to replace serum that is commonly used in cell culture. Agonists are thus useful in specifically promoting the growth and/or development of cells of the myeloid and lymphoid lineages in culture. Additionally, Zzp1 polypeptides and Zzp1 agonists, including small molecules are useful as a research reagent, such as for the expansion, differentiation, and/or cell-cell interactions of pituitary, thymus, brain, testis, ovary, prostate, salivary gland, small intestine, islet, and placenta. Zzp1 polypeptides are added to tissue culture media for these cell types.

Antagonists are also useful as research reagents for characterizing sites of interactions between members of complement/anti-complement pairs as well as sites of cell-cell interactions. Inhibitors of Zzp1 activity (Zzp1 antagonists) include anti-Zzp1 antibodies and soluble Zzp1 polypeptides (such as in SEQ ID NO:2), as well as other peptidic and non-peptidic agents (including ribozymes).

Zzp1 can also be used to identify inhibitors (antagonists) of its activity. Test compounds are added to the assays disclosed herein to identify compounds that inhibit the activity of Zzp1. In addition to those assays disclosed herein, samples can be tested for inhibition of Zzp1 activity within a variety of assays designed to measure sperm-receptor binding or the stimulation/inhibition of Zzp1-dependent cellular responses. For example, Zzp1-responsive cell lines can be transfected with a reporter gene construct that is responsive to a Zzp1-stimulated cellular pathway. Reporter gene constructs of this type are known in the art, and will generally comprise a DNA response element operably linked to a gene encoding an assayable protein, such as luciferase, or a metabolite, such as cyclic AMP. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of Zzp1 on the target cells, as evidenced by a decrease in Zzp1 stimulation of reporter gene expression. Assays of this type will detect compounds that directly block Zzp1 binding to ligand, i.e., sperm, or the anti-complementary member of a complementary/anti-complementary pair, as well as compounds that block processes in the cellular pathway subsequent to complement/anti-complement binding. In the alternative, compounds or other samples can be tested for direct blocking of Zzp1 binding to a sperm using Zzp1 tagged with a detectable label (e.g., $^{125}$I, biotin, horseradish peroxidase, FITC, and the like). Within assays of this type, the ability of a test sample to inhibit the binding of labeled Zzp1 to the sperm is indicative of inhibitory activity, which can be confirmed through secondary assays.

Polypeptides of Zzp1, its agonist or antagonists can also be used to induce transient or permanent sterility. Thus, the polypeptides of the present invention, or portions thereof, can be administered to an animal, to act as an agonist of sperm binding, or to induce an immune response such that the sperm is unable to bind to the egg, or such that the sperm-egg binding event does not result in fertilization. Such polypeptides, agonists, and antagonists can be in recombinant, purified form, as part of a mixed cell lysate, in combination with other proteins and/or fusions. Similarly antibodies to the polypeptides of Zzp1 can be administered to an animal, to induce transient or permanent sterility. Modulating fertility in this manner is useful for many genera of animals including, but not limited to, humans, cats, dogs, horses, cows, rabbits, goats, sheep, rodents, and the like.

Also, Zzp1 polypeptides, agonists or antagonists thereof may be therapeutically useful for promoting wound healing, for example, in pituitary, thymus, brain, testis, ovary, prostate, salivary gland, small intestine, islet, and placenta tissues. To verify the presence of this capability in Zzp1 polypeptides, agonists or antagonists of the present invention, such Zzp1 polypeptides, agonists or antagonists are evaluated with respect to their ability to facilitate wound healing according to procedures known in the art. If desired, Zzp1 polypeptide performance in this regard can be compared to growth factors, such as EGF, NGF, TGF-α, TGF-β, insulin, IGF-I, IGF-II, fibroblast growth factor (FGF) and the like. In addition, Zzp1 polypeptides or agonists or antagonists thereof may be evaluated in combination with one or more growth factors to identify synergistic effects.

A Zzp1 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing sperm are passed through the column one or more times to allow sperm to bind to the Zzp1 polypeptide. The sperm is then eluted using changes in salt concentration, chaotropic agents (guanidine HCl), or pH to disrupt sperm-Zzp1 receptor binding.

An assay system that uses a ligand-binding receptor (or an antibody, one member of a complementary/anti-complementary pairor other cell-surface binding protein) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member, zona pellucida or fragment is covalently attached, using amine or sulflhydryl chemistry, to dextran fibers that are attached to gold film within the flow cell. A test sample is passed through the cell. If a sperm, epitope, or opposite member of the complementary/anti-complementary pair is present in the sample, it will bind to the immobilized Zzp1, antibody or member, respectively, causing a change in the refractive index of the medium, which is detected as a change in surface plasmon resonance of the gold film. This system allows the determination of on- and off-rates, from which binding affinity can be calculated, and assessment of stoichiometry and binding.

Polypeptides, and polypeptide fragments, which bind Zzp1 polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

A "soluble protein" is a protein that is not bound to a cell membrane. Soluble proteins are most commonly ligand-binding receptor polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively.

Soluble forms of the Zzp1 polypeptides include the amino acid sequence from residue 1 to residue 548 to SEQ ID NO:2; from residue 1 to residue 549; from residue 1 to residue 550; from residue 1 to residue 551; from residue 1 to residue 552; from residue 1 to residue 592; from residue 26 to residue 548 to SEQ ID NO:2; from residue 26 to residue 549; from residue 26 to residue 550; from residue 26 to residue 551; from residue 26 to residue 552; and from residue 26 to residue 592; and fragments thereof. Soluble forms of Zzp1 polypeptides, such as the polypeptide of SEQ ID NOs:2, may act as antagonsits to or agonists of Zzp1 polypeptides, and would be useful to modulate the effects of Zzp1 pituitary, thymus, brain, testis, ovary, prostate, salivary gland, small intestine, islet, and placenta. Thus, a polypeptide of Zzp1 that does not contain a transmembrane domain (i.e., the polypeptides of SEQ ID NO:2) will be soluble, and may act as an agonist or antagonist of Zzp1 activity. Since polypeptides of this nature are not anchored to the membrane, they can act at sites distant from the tissues in which they are expressed. Thus, the activity of the soluble form of Zzp1 polypeptides can be more wide spread than its membrane-anchored counterpart. Both forms would be useful in studying the effects of the present invention in vitro an in vivo.

Molecules of the present invention can be used to identify and isolate sperm cells, or cells expressing ZP2 and ZP3, or members of complement/anti-complement pairs involved in fertilization. For example, proteins and peptides of the present invention can be immobilized on a column and membrane preparations run over the column (*Immobilized Affinity Ligand Techniques*, Hermanson et al., eds., Academic Press, San Diego, Calif., 1992, pp. 195–202). Proteins and peptides can also be radiolabeled (*Methods in Enzymol.*, vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cell-surface proteins can be identified.

The molecules of the present invention will be useful in modulating fertility, modulating immunologic recognition, gamete maturation, and/or extracellular matrix formation. The polypeptides, nucleic acid and/or antibodies of the present invention can be used in treatment of disorders associated with infertility. The molecules of the present invention can be used to modulate fertilization or to treat or prevent development of pathological conditions in such diverse tissue as testes, pituitary, thymus, brain, testis, ovary, prostate, salivary gland, small intestine, islet, and placenta. In particular, certain diseases may be amenable to such diagnosis, treatment or prevention. The molecules of the present invention can be used to modulate inhibition and proliferation of neurons and myocytes in pituitary, thymus, brain, testis, ovary, prostate, salivary gland, small intestine, islet, and placenta. Disorders which may be amenable to diagnosis, treatment or prevention with Zzp1 polypeptides include, for example, Alzheimers's Disease, tumor formation, Multiple Sclerosis, Congestive Heart Failure, Ischemic Reperfusion or infarct, and degenerative diseases.

Polynucleotides encoding Zzp1 polypeptides are useful within gene therapy applications where it is desired to increase or inhibit Zzp1 activity. If a mammal has a mutated or absent Zzp1 gene, the Zzp1 gene can be introduced into the cells of the mammal. In one embodiment, a gene encoding a Zzp1 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a Zzp1 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Similarly, the Zzp1 polynucleotides (SEQ ID NO:1) can be used to target specific tissues such as pituitary, thymus, brain, testis, ovary, prostate, salivary gland, small intestine, islet, and placenta. It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Various techniques, including antisense and ribozyme methodologies, can be used to inhibit Zzp1 gene transcription and translation, such as to inhibit cell proliferation in vivo. Polynucleotides that are complementary to a segment of a Zzp1-encoding polynucleotide (e.g., a polynucleotide as set forth in SEQ ID NO:1) are designed to bind to Zzp1-encoding mRNA and to inhibit translation of such mRNA. Such antisense polynucleotides are used to inhibit expression of Zzp1 polypeptide-encoding genes in cell culture or in a subject.

Mice engineered to express the Zzp1 gene, referred to as "transgenic mice," and mice that exhibit a complete absence of Zzp1 gene function, referred to as "knockout mice," may also be generated (Snouwaert et al., *Science* 257:1083, 1992), may also be generated (Lowell et al., *Nature* 366:740–42, 1993; Capecchi, M. R., *Science* 244: 1288–1292, 1989; Palmiter, R. D. et al. *Annu Rev Genet.* 20: 465–499, 1986). For example, transgenic mice that overexpress Zzp1, either ubiquitously or under a tissue-specific or tissue-restricted promoter can be used to ask whether over-expression causes a phenotype. For example, over-expression of a wild-type Zzp1 polypeptide, polypeptide fragment or a mutant thereof may alter normal cellular processes, resulting in a phenotype that identifies a tissue in which Zzp1 expression is functionally relevant and may indicate a therapeutic target for the Zzp1, its agonists or antagonists. For example, a transgenic mouse to engineer is one that over-expresses the soluble Zzp1 polypeptide (approximately amino acids 26 to 246 of SEQ ID NO:2, or approximately amino acids 26 to 627 of SEQ ID NO:2). Moreover, such over-expression may result in a phenotype that shows similarity with human diseases. Similarly, knockout Zzp1 mice can be used to determine where, or at what stage Zzp1 is absolutely required in vivo. The phenotype of knockout mice is predictive of the in vivo effects of that a Zzp1 antagonist, such as those described herein, may have. The human Zzp1 cDNA can be used to isolate murine Zzp1 mRNA, cDNA and genomic DNA, which are subsequently used to generate knockout mice. These mice may be employed to study the Zzp1 gene and the protein encoded thereby in an in vivo system, and can be used as in vivo models for corresponding human diseases. Moreover, transgenic mice expression of Zzp1 antisense polynucleotides or ribozymes directed against Zzp1, described herein, can be used analogously to transgenic mice described above.

Zzp1 polypeptides, variants, and fragments thereof, may be useful as replacement therapy for disorders associated with, for example, fertility, gamete maturation, and immunology.

A less widely appreciated determinant of tissue morphogenesis is the process of cell rearrangement: Both cell motility and cell-cell adhesion are likely to play central roles in morphogenetic cell rearrangements. Cells need to be able to rapidly break and probably simultaneously remake contacts with neighboring cells. See Gumbiner, B. M., *Cell* 69:385–387, 1992. As a secreted protein in pituitary, thymus, brain, testis, ovary, prostate, salivary gland, small intestine, islet, and placenta, Zzp1 can play a role in intercellular rearrangement in these and other tissues.

Zzp1 gene may be useful to as a probe to identify humans who have a defective Zzp1 gene. The presence of Zzp1 polynucleotides in pituitary, thymus, brain, testis, ovary, prostate, salivary gland, small intestine, islet, and placenta suggests that Zzp1 polynucleotides or polypeptides can be used as measured as an indication of aberrant growth in these tissues. Thus, polynucleotides and polypeptides of Zzp1, and mutations to them, can be used a diagnostic indicators of cancer in these tissues.

The polypeptides of the present invention are useful in studying cell adhesion and the role thereof in metastasis and may be useful in preventing metastasis, in particular metastasis in tumors of the pituitary, thymus, brain, testis, ovary, prostate, salivary gland, small intestine, islet, and placenta. Similarly, polynucleotides and polypeptides of Zzp1 may be used to replace their defective counterparts in tumor or malignant tissues.

The Zzp1 polypeptide is expressed in the pituitary, thymus, brain, testis, ovary, prostate, salivary gland, small intestine, islet, and placenta. Thus, Zzp1 polypeptide pharmaceutical compositions of the present invention may be useful in prevention or treatment of disorders associated with pathological regulation or the expansion of pituitary, thymus, brain, testis, ovary, prostate, salivary gland, small intestine, islet, and placenta.

In consideration of the strong expression of Zzp1 in pituitary, thymus, brain, testis, ovary, prostate, salivary gland, small intestine, islet, and placenta and the similarity of the zona pellucida domain to that of ZP2 and ZP3 suggest a role in reproduction for Zzp1 polypeptides and polynucleotides. Thus Zzp1 can be used to study sperm-egg fusion in vitro.

The polynucleotides of the present invention may also be used in conjunction with a regulatable promoter, thus allowing the dosage of delivered protein to be regulated.

The Zzp1 polynucleotides of SEQ ID NO:2 have been mapped to chromosome 11q13. Thus, the present invention also provides reagents which will find use in diagnostic applications. For example, the Zzp1 gene, a probe comprising Zzp1 DNA or RNA or a subsequence thereof can be used to determine if the Zzp1 gene is present on chromosome 11q13 or if a mutation has occurred. Detectable chromosomal aberrations at the Zzp1 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

For pharmaceutical use, the proteins of the present invention can be administered orally, rectally, parenterally (particularly intravenous or subcutaneous), intracisternally, intravaginally, intraperitoneally, topically (as powders, ointments, drops or transdermal patch) bucally, or as a pulmonary or nasal inhalant. Intravenous administration will be by bolus injection or infusion over a typical period of one to several hours. In general, pharmaceutical formulations will include a Zzp1 protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 $\mu$g/kg of patient weight per day, preferably 0.5–20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of Zzp1 is an amount sufficient to produce a clinically significant change in extracellular matrix remodeling, scar tissue formation, tumor suppression, platelet aggregation, apoptosis, myogenesis, in pituitary, thymus, brain, testis, ovary, prostate, salivary gland, small intestine, islet, and placenta tissues. Similarly, a therapeutically effective amount of Zzp1 is an amount sufficient to produce a clinically significant change in disorders associated with ovary, brain, testis, pituitary, thymus, and oocytes and embryos.

The invention is further illustrated by the following non-limiting examples.

EXAMPLES

Example 1

Tissue Distribution in Tissue Panels Using PCR

A panel of cDNAs from human tissues was screened for zzp1 expression using PCR. The panel was made in-house and contained 78 cDNA samples from marathon cDNA and cDNA samples from various normal and cancerous human tissues and cell lines as shown in Table 4, below. The cDNA samples came from in-house libraries or marathon cDNA preparations of RNA that were prepared in-house, or from a commercial supplier such as Clontech (Palo Alto, Calif.) or Invitrogen (Carlsbad, Calif.). The marathon cDNAs were made using the Marathon-Ready™ Kit (Clontech, Palo Alto, Calif.) and standardized to ensure an equal amount of cDNA was placed into each well. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA; and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2–100 pg/$\mu$l of cDNA. The PCR reactions were set up using oligos ZC29717 (SEQ ID NO: 4) and ZC29869 (SEQ ID NO: 5), TaKaRa Ex Taq™ (TAKARA Shuzo Co LTD, Biomedicals Group, Japan), and Rediload dye (Research Genetics, Inc., Huntsville, Ala.). The amplification was carried out as follows: 1 cycle at 94° C. for 2 minutes, 35 cycles of 94° C. for 30 seconds, 61.1° C. for 30 seconds and 72° C. for 30 seconds, followed by 1 cycle at 72° C. for 5 minutes. About 10 $\mu$l of the PCR reaction product was subjected to standard Agarose gel electrophoresis using a 4% agarose gel. The correct DNA fragment size of ~232 bp was observed in pituitary, prostate, salivary gland, small intestine, testis, islet, placenta and genomic. Genomic band larger then other samples bands.

The DNA fragments for 3 testis samples and islet were excised and purified using a Gel Extraction Kit (Qiagen, Chatsworth, Calif.) according to manufacturer's instructions. Fragments were confirmed by sequencing to show that they were indeed zzp1.

TABLE 4

| Tissue/Cell line | #tested | Tissue/Cell line | #tested |
|---|---|---|---|
| Adrenal gland | 1 | Bone marrow | 2 |
| Bladder | 1 | Fetal brain | 2 |
| Bone Marrow | 1 | Islet | 1 |
| Brain | 1 | Prostate | 2 |
| Cervix | 1 | RPMI #1788 (ATCC # CCL-156) | 2 |

TABLE 4-continued

| Tissue/Cell line | #tested | Tissue/Cell line | #tested |
|---|---|---|---|
| Colon | 1 | Testis | 3 |
| Fetal brain | 1 | Thyroid | 1 |
| Fetal heart | 2 | WI38 (ATCC # CCL-75) | 1 |
| Fetal kidney | 1 | Spinal cord | 1 |
| Fetal liver | 1 | HaCat - human keratinocytes | 1 |
| Fetal lung | 1 | HPV (ATCC # CRL-2221) | 1 |
| Fetal muscle | 1 | MG63 | 1 |
| Fetal skin | 1 | Prostate SM | 1 |
| Heart | 2 | CD3 + selected PBMC's Ionomycin + PMA stimulated | 1 |
| K562 (ATCC # CCL-243) | 1 | HPVS (ATCC # CRL-2221) - selected | 1 |
| Kidney | 1 | Heart | 1 |
| Liver | 1 | Pituitary | 1 |
| Lung | 1 | Placenta | 2 |
| Lymph node | 1 | Salivary gland | 1 |
| Melanoma | 1 | Mammary gland | 1 |
| Pancreas | 1 | Ovary | 1 |
| Pituitary | 1 | Adipocyte 1 | 1 |
| Placenta | 1 | Esophagus tumor | 1 |
| Prostate | 1 | Stomach tumor | 1 |
| Rectum | 1 | Liver tumor | 1 |
| Salivary Gland | 1 | Lung tumor | 1 |
| Skeletal muscle | 1 | Ovarian tumor | 1 |
| Small intestine | 1 | Rectal tumor | 1 |
| Spinal cord | 1 | Uterus tumor | 2 |
| Spleen | 1 | | |
| Stomach | 1 | | |
| Testis | 2 | | |
| Thymus | 1 | | |
| Thyroid | 1 | | |
| Trachea | 1 | | |
| Uterus | 1 | | |

Example 2

Zzp1 Protein Production

E. coli, Pichia, Baculovirus, CHO and BHK cells are transfected with expression vectors containing the DNA sequence of SEQ ID NO:1, or a portion thereof. The procedure described below is used for protein expressed in conditioned medium of E. coli, Pichia methanolica, and Chinese hamster ovary (CHO) and baby hamster kidney (BHK) cells. For Zzp1 expressed in E. coli and Pichia, however, the medium is not concentrated prior to purification. Unless otherwise noted, all operations are carried out at 4° C. A total of 25 liters of conditioned medium from BHK cells is sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) S10Y3 membrane. The concentrated material is again sterile-filtered with the Gelman filter as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A combination of procedures including, but not limited to, anion and cation exchange chromatography, size exclusion, and affinity chromography is used to purify untagged Zzp1.

Example 3

Contraceptive Immunizations

Primates are immunized with Zzp1 as follows:

Zzp1 polypeptides, or fragments thereof, which are expressed and purified as taught herein, are used to immunize mammals to induce transient or permanent sterility. Vaccinations are made with Zzp1 proteins and are administered alone or in combination therapy with another zona pelucida protein. Exemplary amounts of protein used in the vaccination is between 250 and 500 micrograms of protein combined with an adjuvant to a total volume of one milliliter. The particular adjuvant can be a well-known adjuvant such as Fruend's complete adjuvant, modified Freund's adjuvant, or other adjuvants known in the art, and include Keyhole limpet hemocyanin, and muramyl dipeptide, for example. One or more vaccinations are administered to prevent pregnancy. Administration of the vaccine can be used to induce autoimmunity which results in loss of oocytes and permanent sterility. Alternatively, the vaccine can be used as a periodic booster to maintain transient sterility.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide molecule comprising residues 26 to 546 of SEQ ID NO:2.

2. The isolated polypeptide molecule according to claim 1, wherein the polypeptide molecule comprises residues 26 to 627 of SEQ ID NO:2.

3. The isolated polypeptide molecule according to claim 1, wherein the polypeptide molecule comprises residues 1 to 627 of SEQ ID NO:2.

4. The isolated polypeptide molecule of claim 1, wherein the polypeptide is operably linked via a peptide bond or polypeptide linker to a second polypeptide selected from the group consisting of maltose binding protein, an immunoglobulin constant region, and a polyhistidine tag.

5. The isolated polypeptide molecule according to claim 1, wherein the polypeptide comprises a fusion protein wherein polypeptide is conjugated with a compound selected from the group consisting of keyhole limpet hemocyanin, muramyl dipeptide, histidine-tag, beta gal, and palmitic acid.

6. A polypeptide produced by the method of culturing a cell containing an expression vector, wherein the expression vector comprises the following operably linked elements:

a) a transcription promoter;

b) a DNA segment encoding the polypeptide according to claim 1; and c) a transcription terminator;

whereby said cell expresses the polypeptide encoded by the DNA segment, and recovering the polypeptide.

7. A composition comprising a contraceptive dose of the polypeptide according to claim 1, and an acceptable carrier, and/or adjuvant.

* * * * *

SEQUENCE LISTING

```
<160> NUMBER OF SEQ ID NOS: 5

<210> SEQ ID NO 1
<211> LENGTH: 1908
<212> TYPE: DNA
<213> ORGANISM: Homo sapiens
<220> FEATURE:
<221> NAME/KEY: CDS
<222> LOCATION: (1)...(1908)

<400> SEQUENCE: 1 atg gca gga ggc tca gcc acg acc tgg ggt tac cct gtg gcc ctg cta      48
Met Ala Gly Gly Ser Ala Thr Thr Trp Gly Tyr Pro Val Ala Leu Leu
1               5                   10                  15 ctg ctg gtt gcc acc ctg ggg ctg ggt agg tgg ctc cag ccc gac cca      96
Leu Leu Val Ala Thr Leu Gly Leu Gly Arg Trp Leu Gln Pro Asp Pro
                20                  25                  30 ggc ctc cgg cac agc tac gac tgt ggg atc aag gga atg cag ctg ctg     144
Gly Leu Arg His Ser Tyr Asp Cys Gly Ile Lys Gly Met Gln Leu Leu
            35                  40                  45 gtg ttc ccc agg cca ggc cag act ctc cgc ttc aag gtg gtg gat gaa     192
Val Phe Pro Arg Pro Gly Gln Thr Leu Arg Phe Lys Val Val Asp Glu
        50                  55                  60 ttt ggg aac cga ttt gat gtc aac aac tgc tcc atc tgc tac cac tgg     240
Phe Gly Asn Arg Phe Asp Val Asn Asn Cys Ser Ile Cys Tyr His Trp
65                  70                  75                  80 gtc acc tcc agg ccg cag gag cct gca gtc ttc tcg gcc gat tac aga     288
Val Thr Ser Arg Pro Gln Glu Pro Ala Val Phe Ser Ala Asp Tyr Arg
                85                  90                  95 ggc tgc cac gtg ctg gag aag gat ggg cgt ttc cac ctg agg gtg ttc     336
Gly Cys His Val Leu Glu Lys Asp Gly Arg Phe His Leu Arg Val Phe
            100                 105                 110 atg gag gct gtg ctg ccc aat ggt cgt gtg gat gtg gca caa gac gct     384
Met Glu Ala Val Leu Pro Asn Gly Arg Val Asp Val Ala Gln Asp Ala
        115                 120                 125 act ctg atc tgt ccc aaa cct gac ccc tcc cgg act ctg gac tcc cag     432
Thr Leu Ile Cys Pro Lys Pro Asp Pro Ser Arg Thr Leu Asp Ser Gln
    130                 135                 140 ctg gca cca ccc gcc atg ttc tct gtc tca acc cca caa acc ctt tcc     480
Leu Ala Pro Pro Ala Met Phe Ser Val Ser Thr Pro Gln Thr Leu Ser
145                 150                 155                 160 ttc ctc ccc acc tct ggc cat acc tcc caa ggc tct ggc cat gcc ttt     528
Phe Leu Pro Thr Ser Gly His Thr Ser Gln Gly Ser Gly His Ala Phe
                165                 170                 175
```

```
ccc agc cca ctg gac cca ggg cac agc tct gtc cac cca acc cct gct         576
Pro Ser Pro Leu Asp Pro Gly His Ser Ser Val His Pro Thr Pro Ala
            180                 185                 190 tta cca tcc cct gga cct gga cct acc ctc gcc acc ctg gct caa ccc         624
Leu Pro Ser Pro Gly Pro Gly Pro Thr Leu Ala Thr Leu Ala Gln Pro
        195                 200                 205 cac tgg ggc acc ttg gaa cac tgg gat gtg aac aaa cga gat tac ata         672
His Trp Gly Thr Leu Glu His Trp Asp Val Asn Lys Arg Asp Tyr Ile
    210                 215                 220 ggt acc cac ctg agc cag gag cag tgc cag gtg gcc tca ggg cac ctc         720
Gly Thr His Leu Ser Gln Glu Gln Cys Gln Val Ala Ser Gly His Leu
225                 230                 235                 240 ccc tgc atc gtg aga aga act tca aaa gaa gcc tgt cag cag gct ggc         768
Pro Cys Ile Val Arg Arg Thr Ser Lys Glu Ala Cys Gln Gln Ala Gly
                245                 250                 255 tgc tgc tat gac aac acc aga gag gtt ccc tgt tac tat ggc aac aca         816
Cys Cys Tyr Asp Asn Thr Arg Glu Val Pro Cys Tyr Tyr Gly Asn Thr
            260                 265                 270 gct act gtc cag tgc ttc aga gat ggc tac ttc gtc ctc gta gtg tcc         864
Ala Thr Val Gln Cys Phe Arg Asp Gly Tyr Phe Val Leu Val Val Ser
        275                 280                 285 caa gaa atg gcc ttg aca cac agg atc aca ctg gcc aac atc cac ctg         912
Gln Glu Met Ala Leu Thr His Arg Ile Thr Leu Ala Asn Ile His Leu
    290                 295                 300 gcc tat gcc ccc acc agc tgc tcc cca aca cag cac acg gaa gct ttc         960
Ala Tyr Ala Pro Thr Ser Cys Ser Pro Thr Gln His Thr Glu Ala Phe
305                 310                 315                 320 gtg gtc ttc tac ttc cct ctc acc cac tgt gga acc aca atg cag gtg        1008
Val Val Phe Tyr Phe Pro Leu Thr His Cys Gly Thr Thr Met Gln Val
                325                 330                 335 gct ggc gac cag ctc atc tat gag aac tgg ctg gtg tct ggc atc cac        1056
Ala Gly Asp Gln Leu Ile Tyr Glu Asn Trp Leu Val Ser Gly Ile His
            340                 345                 350 atc caa aag ggg cca cag ggt tcc atc acg cgg gac agc acc ttc cag        1104
Ile Gln Lys Gly Pro Gln Gly Ser Ile Thr Arg Asp Ser Thr Phe Gln
        355                 360                 365 ctt cat gtg cgc tgt gtc ttc aac gcc agt gac ttc ctg ccc att cag        1152
Leu His Val Arg Cys Val Phe Asn Ala Ser Asp Phe Leu Pro Ile Gln
    370                 375                 380 gca tcc att ttc cca ccc cca tcg cct gct cct atg acc cag ccc ggc        1200
Ala Ser Ile Phe Pro Pro Pro Ser Pro Ala Pro Met Thr Gln Pro Gly
385                 390                 395                 400 ccc ctg cgg ctt gag ctg cgg att gcc aaa gac gag acc tgc agc tcg        1248
Pro Leu Arg Leu Glu Leu Arg Ile Ala Lys Asp Glu Thr Cys Ser Ser
                405                 410                 415 tac tat ggg gag gat gac tat ccc atc gtg agg ctg ctc cga gaa cca        1296
Tyr Tyr Gly Glu Asp Asp Tyr Pro Ile Val Arg Leu Leu Arg Glu Pro
            420                 425                 430 gtc cat gtg gag gtc cgg ctt ctg cag agg aca gac ccc aac ctg gtc        1344
Val His Val Glu Val Arg Leu Leu Gln Arg Thr Asp Pro Asn Leu Val
        435                 440                 445 ctg ctg ctg cac cag tgc tgg ggc gct ccc agt gcc aac ccc ttc cag        1392
Leu Leu Leu His Gln Cys Trp Gly Ala Pro Ser Ala Asn Pro Phe Gln
    450                 455                 460 cag ccc cag tgg ccc atc ctg tca gac ggc tgc cct ttc aag ggc gac        1440
Gln Pro Gln Trp Pro Ile Leu Ser Asp Gly Cys Pro Phe Lys Gly Asp
465                 470                 475                 480 agc tac aga acc caa atg gta gcc ttg gac ggg gcc aca cct ttc cag        1488
Ser Tyr Arg Thr Gln Met Val Ala Leu Asp Gly Ala Thr Pro Phe Gln
                485                 490                 495
```

-continued

```
tcg cac tac cag cga ttc act gtt gct acc ttc gcc ctc ctg gac tca      1536
Ser His Tyr Gln Arg Phe Thr Val Ala Thr Phe Ala Leu Leu Asp Ser
            500                 505                 510 ggc tcc cag aga gcc ctc aga gga ctg gtt tac ttg ttc tgc agc acc      1584
Gly Ser Gln Arg Ala Leu Arg Gly Leu Val Tyr Leu Phe Cys Ser Thr
        515                 520                 525 tct gcc tgc cac acc tca ggg ctg gag act tgc tcc act gca tgt agc      1632
Ser Ala Cys His Thr Ser Gly Leu Glu Thr Cys Ser Thr Ala Cys Ser
    530                 535                 540 act ggc act aca aga cag cga cga tcc tca ggt cac cgt aat gac act      1680
Thr Gly Thr Thr Arg Gln Arg Arg Ser Ser Gly His Arg Asn Asp Thr
545                 550                 555                 560 gcc agg ccc cag gac atc gtg agc tct ccg ggg cca gtg ggc ttt gag      1728
Ala Arg Pro Gln Asp Ile Val Ser Ser Pro Gly Pro Val Gly Phe Glu
                565                 570                 575 gat tct tat ggg cag gag ccc aca ctt ggg ccc aca gac tcc aat ggg      1776
Asp Ser Tyr Gly Gln Glu Pro Thr Leu Gly Pro Thr Asp Ser Asn Gly
            580                 585                 590 aac tcc agc ctg aga cct ctc ctt tgg gcg gtc ctt ttg ctg cca gct      1824
Asn Ser Ser Leu Arg Pro Leu Leu Trp Ala Val Leu Leu Leu Pro Ala
        595                 600                 605 gtt gcc ctg gtc ctt ggg ttt ggt gtc ttt gtg ggc ctg agc cag acc      1872
Val Ala Leu Val Leu Gly Phe Gly Val Phe Val Gly Leu Ser Gln Thr
    610                 615                 620 tgg gcc cag aag ctc tgg gaa agc aac aga cag tga                      1908
Trp Ala Gln Lys Leu Trp Glu Ser Asn Arg Gln *
625                 630                 635

<210> SEQ ID NO 2
<211> LENGTH: 635
<212> TYPE: PRT
<213> ORGANISM: Homo sapiens

<400> SEQUENCE: 2

Met Ala Gly Gly Ser Ala Thr Thr Trp Gly Tyr Pro Val Ala Leu Leu
 1               5                  10                  15

Leu Leu Val Ala Thr Leu Gly Leu Gly Arg Trp Leu Gln Pro Asp Pro
            20                  25                  30

Gly Leu Arg His Ser Tyr Asp Cys Gly Ile Lys Gly Met Gln Leu Leu
        35                  40                  45

Val Phe Pro Arg Pro Gly Gln Thr Leu Arg Phe Lys Val Val Asp Glu
    50                  55                  60

Phe Gly Asn Arg Phe Asp Val Asn Asn Cys Ser Ile Cys Tyr His Trp
65                  70                  75                  80

Val Thr Ser Arg Pro Gln Glu Pro Ala Val Phe Ser Ala Asp Tyr Arg
                85                  90                  95

Gly Cys His Val Leu Glu Lys Asp Gly Arg Phe His Leu Arg Val Phe
            100                 105                 110

Met Glu Ala Val Leu Pro Asn Gly Arg Val Asp Val Ala Gln Asp Ala
        115                 120                 125

Thr Leu Ile Cys Pro Lys Pro Asp Pro Ser Arg Thr Leu Asp Ser Gln
    130                 135                 140

Leu Ala Pro Pro Ala Met Phe Ser Val Ser Thr Pro Gln Thr Leu Ser
145                 150                 155                 160

Phe Leu Pro Thr Ser Gly His Thr Ser Gln Gly Ser Gly His Ala Phe
                165                 170                 175

Pro Ser Pro Leu Asp Pro Gly His Ser Ser Val His Pro Thr Pro Ala
            180                 185                 190
```

```
Leu Pro Ser Pro Gly Pro Gly Pro Thr Leu Ala Thr Leu Ala Gln Pro
        195                 200                 205

His Trp Gly Thr Leu Glu His Trp Asp Val Asn Lys Arg Asp Tyr Ile
        210                 215                 220

Gly Thr His Leu Ser Gln Glu Gln Cys Gln Val Ala Ser Gly His Leu
225                 230                 235                 240

Pro Cys Ile Val Arg Arg Thr Ser Lys Glu Ala Cys Gln Gln Ala Gly
                245                 250                 255

Cys Cys Tyr Asp Asn Thr Arg Glu Val Pro Cys Tyr Tyr Gly Asn Thr
                260                 265                 270

Ala Thr Val Gln Cys Phe Arg Asp Gly Tyr Phe Val Leu Val Val Ser
        275                 280                 285

Gln Glu Met Ala Leu Thr His Arg Ile Thr Leu Ala Asn Ile His Leu
        290                 295                 300

Ala Tyr Ala Pro Thr Ser Cys Ser Pro Thr Gln His Thr Glu Ala Phe
305                 310                 315                 320

Val Val Phe Tyr Phe Pro Leu Thr His Cys Gly Thr Thr Met Gln Val
                325                 330                 335

Ala Gly Asp Gln Leu Ile Tyr Glu Asn Trp Leu Val Ser Gly Ile His
        340                 345                 350

Ile Gln Lys Gly Pro Gln Gly Ser Ile Thr Arg Asp Ser Thr Phe Gln
        355                 360                 365

Leu His Val Arg Cys Val Phe Asn Ala Ser Asp Phe Leu Pro Ile Gln
        370                 375                 380

Ala Ser Ile Phe Pro Pro Ser Pro Ala Pro Met Thr Gln Pro Gly
385                 390                 395                 400

Pro Leu Arg Leu Glu Leu Arg Ile Ala Lys Asp Glu Thr Cys Ser Ser
                405                 410                 415

Tyr Tyr Gly Glu Asp Asp Tyr Pro Ile Val Arg Leu Arg Glu Pro
                420                 425                 430

Val His Val Glu Val Arg Leu Gln Arg Thr Asp Pro Asn Leu Val
        435                 440                 445

Leu Leu Leu His Gln Cys Trp Gly Ala Pro Ser Ala Asn Pro Phe Gln
        450                 455                 460

Gln Pro Gln Trp Pro Ile Leu Ser Asp Gly Cys Pro Phe Lys Gly Asp
465                 470                 475                 480

Ser Tyr Arg Thr Gln Met Val Ala Leu Asp Gly Ala Thr Pro Phe Gln
                485                 490                 495

Ser His Tyr Gln Arg Phe Thr Val Ala Thr Phe Ala Leu Leu Asp Ser
                500                 505                 510

Gly Ser Gln Arg Ala Leu Arg Gly Leu Val Tyr Leu Phe Cys Ser Thr
        515                 520                 525

Ser Ala Cys His Thr Ser Gly Leu Glu Thr Cys Ser Thr Ala Cys Ser
        530                 535                 540

Thr Gly Thr Thr Arg Gln Arg Ser Ser Gly His Arg Asn Asp Thr
545                 550                 555                 560

Ala Arg Pro Gln Asp Ile Val Ser Ser Pro Gly Pro Val Gly Phe Glu
                565                 570                 575

Asp Ser Tyr Gly Gln Glu Pro Thr Leu Gly Pro Thr Asp Ser Asn Gly
                580                 585                 590

Asn Ser Ser Leu Arg Pro Leu Leu Trp Ala Val Leu Leu Leu Pro Ala
        595                 600                 605
```

```
Val Ala Leu Val Leu Gly Phe Gly Val Phe Val Gly Leu Ser Gln Thr
    610                 615                 620
Trp Ala Gln Lys Leu Trp Glu Ser Asn Arg Gln
625                 630                 635

<210> SEQ ID NO 3
<211> LENGTH: 1905
<212> TYPE: DNA
<213> ORGANISM: Artificial Sequence
<220> FEATURE:
<223> OTHER INFORMATION: degenerate nucleotide sequence
<221> NAME/KEY: misc_feature
<222> LOCATION: 6, 9, 12, 15, 18, 21, 24, 30, 36, 39, 42, 45, 48, 51,
      54, 57, 60, 63, 66, 69, 72, 75, 78, 84, 90, 96, 99, 102, 105,
      111, 123, 132, 141, 144, 147, 153, 156, 159, 162, 168, 171,
      174, 183, 186, 198, 204, 213, 225, 243, 246, 249, 252
<223> OTHER INFORMATION: n = A,T,C or G
<221> NAME/KEY: misc_feature
<222> LOCATION: 255, 264, 267, 270, 276, 279, 288, 291, 300, 303, 315,
      318, 327, 330, 333, 345, 348, 351, 354, 360, 363, 366, 372, 375,
      384, 387, 390, 399, 405, 411, 414, 417, 420, 423, 429, 435,
      438, 441, 444, 447, 456, 459, 462, 465, 468, 474, 477
<223> OTHER INFORMATION: n = A,T,C or G
<221> NAME/KEY: misc_feature
<222> LOCATION: 480, 486, 489, 492, 495, 498, 504, 507, 513, 516, 519,
      525, 531, 534, 537, 540, 546, 549, 555, 558, 561, 567, 570, 573,
      576, 579, 582, 585, 588, 591, 594, 597, 600, 603, 606, 609,
      612, 615, 618, 624, 633, 636, 639, 654, 663, 675, 678
<223> OTHER INFORMATION: n = A,T,C or G
<221> NAME/KEY: misc_feature
<222> LOCATION: 684, 687, 705, 708, 711, 714, 720, 723, 732, 735, 738,
      741, 744, 753, 765, 768, 786, 789, 795, 798, 810, 816, 819, 822,
      825, 837, 843, 852, 855, 858, 861, 864, 876, 879, 882, 888,
      894, 897, 900, 912, 915, 921, 924, 927, 930, 936, 939
<223> OTHER INFORMATION: n = A,T,C or G
<221> NAME/KEY: misc_feature
<222> LOCATION: 942, 951, 957, 963, 966, 978, 981, 984, 993, 996, 999,
      1008, 1011, 1014, 1023, 1041, 1044, 1047, 1050, 1068, 1071, 1077,
      1080, 1086, 1089, 1095, 1098, 1107, 1113, 1116, 1122, 1131,
      1134
<223> OTHER INFORMATION: n = A,T,C or G
<221> NAME/KEY: misc_feature
<222> LOCATION: 1143, 1146, 1155, 1158, 1167, 1170, 1173, 1176, 1179,
      1182, 1185, 1191, 1197, 1200, 1203, 1206, 1209, 1212, 1218, 1221,
      1227, 1239, 1245, 1248, 1257, 1272, 1278, 1281, 1284, 1287,
      1290, 1296, 1299, 1305, 1311, 1314, 1317, 1320, 1326
<223> OTHER INFORMATION: n = A,T,C or G
<221> NAME/KEY: misc_feature
<222> LOCATION: 1329, 1335, 1341, 1344, 1347, 1350, 1353, 1368, 1371,
      1374, 1377, 1380, 1386, 1398, 1407, 1413, 1416, 1422, 1428, 1437,
      1443, 1449, 1452, 1461, 1464, 1467, 1473, 1476, 1479, 1482,
      1491, 1503, 1509, 1512, 1515, 1518, 1524, 1527, 1530
<223> OTHER INFORMATION: n = A,T,C or G
<221> NAME/KEY: misc_feature
<222> LOCATION: 1536, 1539, 1542, 1548, 1551, 1554, 1557, 1560, 1563,
      1566, 1572, 1581, 1584, 1587, 1590, 1599, 1602, 1605, 1608, 1614,
      1620, 1623, 1626, 1632, 1635, 1638, 1641, 1644, 1647, 1653,
      1656, 1659, 1662, 1665, 1671, 1680, 1683, 1686, 1689
<223> OTHER INFORMATION: n = A,T,C or G
<221> NAME/KEY: misc_feature
<222> LOCATION: 1701, 1704, 1707, 1710, 1713, 1716, 1719, 1722, 1734,
      1740, 1749, 1752, 1755, 1758, 1761, 1764, 1770, 1776, 1782, 1785,
      1788, 1791, 1794, 1797, 1800, 1806, 1809, 1812, 1815, 1818,
      1821, 1824, 1827, 1830, 1833, 1836, 1839, 1842, 1848
<223> OTHER INFORMATION: n = A,T,C or G
<221> NAME/KEY: misc_feature
<222> LOCATION: 1851, 1857, 1860, 1863, 1866, 1872, 1878, 1887, 1896,
      1902
<223> OTHER INFORMATION: n = A,T,C or G

<400> SEQUENCE: 3
atggcnggng gnwsngcnac nacntggggn tayccngtng cnytnytnyt nytngtngcn      60
acnytnggny tnggnmgntg gytncarccn gayccnggny tnmgncayws ntaygaytgy     120
ggnathaarg gnatgcaryt nytngtntty ccnmgnccng gncaracnyt nmgnttyaar     180
```

-continued

```
gtngtngayg arttyggnaa ymgnttygay gtnaayaayt gywsnathtg ytaycaytgg    240
gtnacnwsnm gnccncarga rccngcngtn ttywsngcng aytaymgngg ntgycaygtn    300
ytngaraarg ayggnmgntt ycayytnmgn gtnttyatgg argcngtnyt nccnaayggn    360
mgngtngayg tngcncarga ygcnacnytn athtgyccna arccngaycc nwsnmgnacn    420
ytngaywsnc arytngcncc nccngcnatg ttywsngtnw snacnccnca racnytnwsn    480
ttyytnccna cnwsnggnca yacnwsncar ggnwsnggnc aygcnttycc nwsnccnytn    540
gayccnggnc aywsnwsngt ncayccnacn ccngcnytnc cnwsnccngg nccnggnccn    600
acnytngcna cnytngcnca rccncaytgg ggnacnytng arcaytggga ygtnaayaar    660
mgngaytaya thggnacnca yytnwsncar garcartgyc argtngcnws nggncayytn    720
ccntgyathg tnmgnmgnac nwsnaargar gcntgycarc argcnggntg ytgytaygay    780
aayacnmgng argtnccntg ytaytayggn aayacngcna cngtncartg yttymgngay    840
ggntayttyg tnytngtngt nwsncargar atggcnytna cncaymgnat hacnytngcn    900
aayathcayy tngcntaygc nccnacnwsn tgywsnccna cncarcayac ngargcntty    960
gtngtnttyt ayttyccnyt nacncaytgy ggnacnacna tgcargtngc nggngaycar   1020
ytnathtayg araaytggyt ngtnwsnggn athcayathc araarggncc ncarggnwsn   1080
athacnmgng aywsnacntt ycarytncay gtnmgntgyg tnttyaaygc nwsngaytty   1140
ytnccnathc argcnwsnat httyccnccn ccnwsnccng cnccnatgac ncarccnggn   1200
ccnytnmgny tngarytnmg nathgcnaar gaygaracnt gywsnwsnta ytayggngar   1260
gaygaytayc cnathgtnmg nytnytnmgn garccngtnc aygtngargt nmgnytnytn   1320
carmgnacng ayccnaayyt ngtnytnytn ytncaycart gytggggngc nccnwsngcn   1380
aayccnttyc arcarccnca rtggccnath ytnwsngayg gntgyccntt yaarggngay   1440
wsntaymgna cncaratggt ngcnytngay ggngcnacnc cnttycarws ncaytaycar   1500
mgnttyacng tngcnacntt ygcnytnytn gaywsnggnw sncarmgngc nytnmgnggn   1560
ytngtntayy tnttytgyws nacnwsngcn tgycayacnw snggnytnga racntgywsn   1620
acngcntgyw snacnggnac nacnmgncar mgnmgnwsnw snggncaymg naaygayacn   1680
gcnmgnccnc argayathgt nwsnwsnccn ggnccngtng gnttygarga ywsntayggn   1740
cargarccna cnytnggncc nacngaywsn aayggnaayw snwsnytnmg nccnytnytn   1800
tgggcngtny tnytnytncc ngcngtngcn ytngtnytng gnttyggngt nttygtnggn   1860
ytnwsncara cntgggcnca raarytntgg garwsnaaym gncar                   1905
```

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer ZC29717

<400> SEQUENCE: 4

```
aaaaggggcc acagggttc                                                  19
```

<210> SEQ ID NO 5
<211> LENGTH: 21
<212> TYPE: DNA
<213> ORGANISM: Artificial Sequence

```
-continued

<220> FEATURE:
<223> OTHER INFORMATION: Oligonucleotide primer, ZC29869

<400> SEQUENCE: 5
tctcggagca gcctcacgat g                                              21
```